US010712172B1

United States Patent
Romrell et al.

(10) Patent No.: US 10,712,172 B1
(45) Date of Patent: Jul. 14, 2020

(54) ACCELEROMETER-BASED SYSTEMS AND METHODS FOR QUANTIFYING STEPS

(71) Applicant: SAVVYSHERPA, LLC, Minneapolis, MN (US)

(72) Inventors: Gregory R. Romrell, Provo, UT (US); Ryan J. H. Brunt, Brooklyn, NY (US); Jon Benjamin Griffith, Minneapolis, MN (US); Joseph Roxas, Talisay (PH)

(73) Assignee: SAVVYSHERPA, LLC, Minneapolis, MN (US)

( * ) Notice: Subject to any disclaimer, the term of this patent is extended or adjusted under 35 U.S.C. 154(b) by 0 days.

(21) Appl. No.: 16/710,014

(22) Filed: Dec. 11, 2019

Related U.S. Application Data

(62) Division of application No. 14/879,718, filed on Oct. 9, 2015, now Pat. No. 10,539,429.

(Continued)

(51) Int. Cl.
*G01C 22/00* (2006.01)
*G01P 13/00* (2006.01)
(Continued)

(52) U.S. Cl.
CPC .......... *G01C 22/006* (2013.01); *A61B 5/0022* (2013.01); *A61B 5/1118* (2013.01); *G01P 13/00* (2013.01); *A61B 2562/0219* (2013.01)

(58) Field of Classification Search
CPC ... G01C 22/006; A61B 5/0022; A61B 5/1118; A61B 2562/0219; G01P 13/00
See application file for complete search history.

(56) References Cited

U.S. PATENT DOCUMENTS 5,976,083 A * 11/1999 Richardson .......... A61B 5/0245
                                                                       482/8
7,463,997 B2    12/2008   Pasolini et al.
(Continued)

OTHER PUBLICATIONS

Brajdic, Agata et al. "Walk Detection and Step Counting on Unconstrained Smartphones," Proceedings of the 2013 ACM International Joint Conference on Pervasive and Ubiquitous Computing, Sep. 8-12, 2013, pp. 225-234, ACM, Zurich, Switzerland.

(Continued)

*Primary Examiner* — Regis J Betsch
(74) *Attorney, Agent, or Firm* — Alston & Bird LLP

(57) ABSTRACT

Systems and methods detect steps from one or more sensed accelerometer signals. Systems comprise an accelerometer and a non-transitory computer readable medium, each of which communicates with a processor. The accelerometer is coupled to an individual and generates outputs received by the processor. The non-transitory computer readable medium stores instructions controlling the processor to perform steps of a method. The processor determines a minimum and a maximum reading for respective time periods. Counted peak heights are maxima that exceed a rest threshold. The rest threshold may be a function of the rest maximum. The processor determines a peak threshold for each time period having a counted peak height. A counted amplitude comprises the difference between the maximum reading and minimum readings of a time period in which the counted peak height exceeds the peak threshold. The processor increments a step counter when a counted amplitude exceeds an amplitude threshold.

6 Claims, 11 Drawing Sheets

Related U.S. Application Data

(60) Provisional application No. 62/106,450, filed on Jan. 22, 2015, provisional application No. 62/074,152, filed on Nov. 3, 2014.

(51) Int. Cl.
*A61B 5/11* (2006.01)
*A61B 5/00* (2006.01)

(56) References Cited

U.S. PATENT DOCUMENTS

| | | |
|---|---|---|
| 9,918,664 B2 | 3/2018 | Blahnik et al. |
| 2013/0191069 A1 | 7/2013 | Ravindran |
| 2014/0188431 A1 | 7/2014 | Barfield |
| 2014/0340219 A1 | 11/2014 | Russell et al. |
| 2015/0127290 A1 | 5/2015 | Plasterer et al. |
| 2016/0101319 A1 | 4/2016 | Tanabe et al. |
| 2018/0202830 A1 | 7/2018 | Zhang et al. |

OTHER PUBLICATIONS

United States Patent and Trademark Office, Final Office Action for U.S. Appl. No. 14/924,855, dated Feb. 21, 2018, (29 pages), USA.
United States Patent and Trademark Office, Final Office Action for U.S. Appl. No. 15/434,502, dated Jan. 16, 2019, (26 pages), USA.
United States Patent and Trademark Office, Final Office Action for U.S. Appl. No. 15/434,502, dated Jun. 20, 2019, (27 pages), USA.
United States Patent and Trademark Office, NonFinal Office Action for U.S. Appl. No. 14/924,855, dated Oct. 5, 2017, (22 pages), USA.
United States Patent and Trademark Office, Notice of Allowance for U.S. Appl. No. 14/879,718, dated Sep. 11, 2019, (9 pages), USA.
U.S. Patent and Trademark Office, NonFinal Office Action for U.S. Appl. No. 16/709,996, dated Mar. 5, 2020, (14 pages), USA.
U.S. Patent and Trademark Office, Notice of Allowance for U.S. Appl. No. 16/709,996, dated Mar. 20, 2020, (12 pages), USA.

\* cited by examiner

Time Periods

Threshold-Determined Segments

Local Minima and Maxima

ACCELEROMETER-BASED SYSTEMS AND METHODS FOR QUANTIFYING STEPS

CROSS-REFERENCE TO RELATED APPLICATIONS

The present application is a division of U.S. patent application Ser. No. 14/879,718 filed Oct. 9, 2015, which claims the benefit of U.S. Provisional App. No. 62/074,152 filed Nov. 3, 2014, and of U.S. Provisional Application No. 62/106,450 filed Jan. 22, 2015, the entire contents of which are hereby incorporated in their entireties by reference.

FIELD OF THE INVENTION

Systems and methods relate to detecting steps using an accelerometer.

BACKGROUND

Physical activity has long been recognized as benefitting health. Physical activity levels can also be an indicator of health. For these reasons, a variety of individuals and institutions are interested in monitoring physical activity. Over the past years, activity trackers have become an increasingly popular way for individuals to monitor their physical activity. An activity tracker typically includes an accelerometer as a means of detecting the physical activity of the individual wearing it. The accelerometer generates a series of outputs that vary according to the magnitude of acceleration the accelerometer detects. Outputs may then be converted into readings that correspond to a particular level of acceleration. A series of readings over time may be viewed as a signal.

Activity trackers use accelerometer signals to quantify physical activity in a variety of units including calories burned, distance traveled, and steps taken. Devices that count steps are referred to, generally, as pedometers, though accelerometer-based step counters are sometimes distinguished from pedometers that count the oscillations of a weight. The initiation of contact between a foot and the ground during a step causes a peak in the acceleration signal from an accelerometer coupled to the individual taking the step. However, not all peaks in the acceleration signal are caused by steps. Peaks that are not caused by steps may be referred to as "noise." Noise may be caused, for instance, by the vibrations of a car or the lack of damping in the accelerometer itself.

One method of filtering out noise is to set an acceleration threshold. Peaks that exceed the threshold are presumed to be caused by steps while readings below the threshold are presumed to be noise. However, the boundary between acceleration caused by step activity and that caused by noise may change substantially depending on factors such as how fast an individual is walking or running, the elasticity of the surface on which the step is taken, and the hardness of the individual's shoe soles.

The graph in FIG. 1 illustrates the shortcomings of a single, fixed threshold. Two samples of accelerometer gait data are superimposed on top of each other. Each sample illustrates two steps taken by an individual. The sample with higher peaks (110) comes from a healthy individual. The sample with the lower peaks (120) comes from a patient after surgery. The time scale on the x axis is in 24ths of a second and the units of acceleration on the y axis are 1/64 of g (g=free-fall acceleration in Earth's gravity). Threshold 1 (130) would record both steps from the healthy individual but would not capture any steps from the post-surgery patient. Threshold 2 (140) records both steps from the post-surgery patient, but counts four steps from the healthy individual when only two steps were actually taken. Threshold 3 (150), just slightly lower than Threshold 2, also records both steps from the post-surgery patient, but counts only one step from the healthy individual. Thus, a fixed threshold does not accurately count steps from both the patient and healthy individual.

SUMMARY

Embodiments include systems and methods for detecting steps from one or more sensed accelerometer signals. Systems comprise an accelerometer and a non-transitory computer readable medium, each of which communicates with a processor. The accelerometer generates outputs received by the processor and is coupled to an individual whose steps are to be detected. The non-transitory computer readable medium stores instructions controlling the processor to perform steps of a method. The processor determines readings from the accelerometer outputs. The determination may be, for example, multiplying each output by a coefficient or processing the accelerometer outputs with a data smoothing function. In some embodiments, a peak height is the greatest reading from a time period. Counted peak heights are those peak heights that exceed a rest threshold. The rest threshold may be determined by receiving readings from the accelerometer when it is at rest for a period of time, identifying the rest maximum (the greatest reading generated during the period of rest), and then determining the rest threshold using the rest maximum. The processor determines a peak threshold for each time period having a counted peak height. The peak threshold comprises a weighted average of two or more counted peak heights. A counted amplitude comprises the difference between the maximum reading and minimum reading during a time period in which the counted peak height exceeds the peak threshold. The processor increments a counter when a counted amplitude exceeds the amplitude threshold for the time period of the counted amplitude. The amplitude threshold for a given time period comprises a weighted average of two or more counted amplitudes. An increment represents a step taken by the individual and the number stored by the counter represents a number of steps taken by the individual.

DETAILED DESCRIPTION

Figure 1:
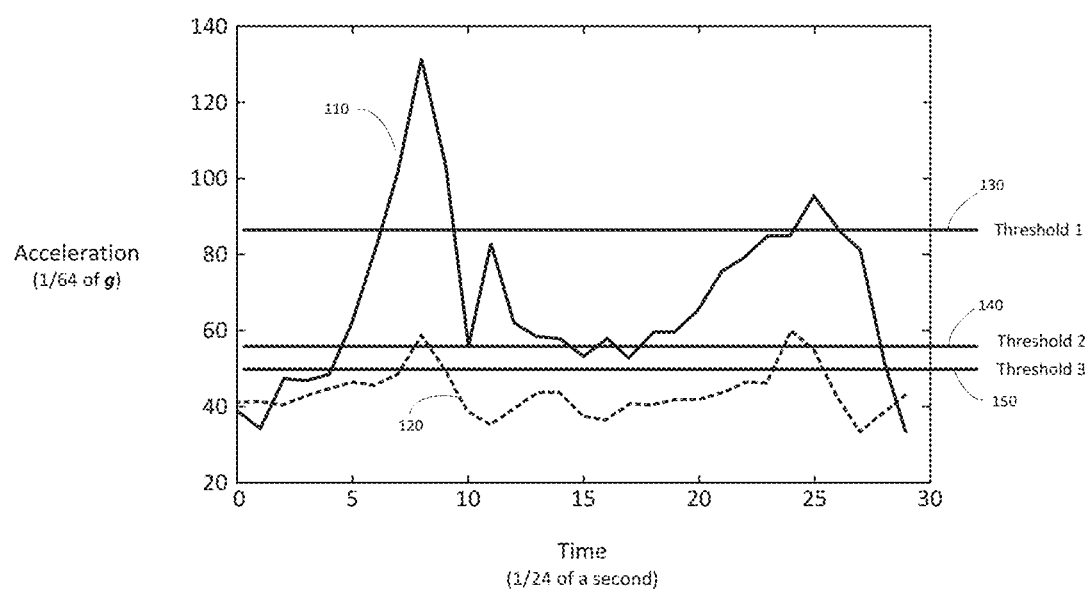
FIG. 1 illustrates the shortcomings of fixed thresholds for counting steps.

Systems and methods detect steps by applying sequential thresholds to one or more sensed accelerometer signals. Sequential thresholds consider signal values that exceeded a first threshold for comparison to a second threshold. In some embodiments, the second threshold may be a function of one or more values that exceeded the first threshold. By sensing changing signal values of the accelerometer readings, the systems and methods dynamically change the thresholds over time.

Systems:

The step-counting methods described herein are performed by a system that includes an accelerometer generating outputs. An accelerometer may refer to any device that measures either linear or angular acceleration, though accelerometers measuring angular acceleration may be referred to as gyroscopes or simply gyros. An accelerometer may refer to a device that measures acceleration in more than one direction. Triaxial accelerometers, for example, measure acceleration on three axes that may be at least approximately orthogonal to one another. In addition to linear and angular acceleration, some accelerometers also contain a magnetometer that can orient accelerations relative to a magnetic field such as Earth's magnetic field. A so-called "9-axis accelerometer" contains a tri-axial accelerometer measuring linear acceleration along three orthogonal axes, angular acceleration around each of the orthogonal axes, and orientation relative to a magnetic field. A 9-axis accelerometer may also be referred to as an inertial measurement unit (IMU).

The accelerometer may be coupled to an individual whose steps are to be measured. Preferred embodiments measure linear acceleration along at least the anterior-posterior axis of the individual, which is approximately vertical when the individual is walking upright. Use of triaxial accelerometers may be advantageous because the accelerometer need not be oriented precisely when coupled to the individual. Summing readings from each of the three axes may produce a signal from which steps may be detected without orienting the accelerometer relative to the individual or to the direction of gravity. Alternatively, for a triaxial accelerometer, the direction of gravity may be deduced from the component of constant acceleration detected at each of the three axes and then virtually oriented relative to gravitational pull.

The accelerometer may be communicatively coupled to a processor. The processor may include one or more processing units. The processor is communicatively coupled to and executes instructions from a computer readable data storage (CRDS) (also referred to herein as a non-transitory computer-readable medium). Embodiments of the CRDS may include random access memory (RAM) and various types of non-volatile memory including, but not limited to, read-only memory (ROM), programmable read-only memory (PROM), erasable programmable read-only memory (EPROM), and electrically erasable programmable read-only memory (EEPROM). Embodiments of the CRDS may include magnetic storage (such as hard drives, floppy disks, and magnetic tape) and/or optical storage (such as CDs and DVDs).

If the method uses time periods, the system may include a means for measuring time. Because processors typically perform calculations on a regular time cycle, some embodiments count processor cycles as a means for measuring time. If the accelerometer generates outputs at regular time intervals, embodiments may count the number of accelerometer outputs to measure the passage of time. Alternatively, a separate time-measuring device may be used to measure time periods. Examples of alternative time measuring devices include electric clocks such as quartz clocks, synchronous clocks, and radio-controlled clocks that are wirelessly synchronized with a time standard such as an atomic clock.

The output of the system is a signal indicating that a step has been taken. The system may store, on the CRDS for example, a tally of the number of steps that have been taken during a specified amount of time. The processor may increment the tally each time a step is detected so that the tally serves as a step counter. The system may also include a means for communicating these results. The communication means may be, for example, a visual display, audio speaker, or tactile output. The system may also include a user interface allowing a user to input information into the computer, for example to display different measures of physical activity.

Certain components of the system may be communicatively coupled to other components. The processor, for instance, may receive information from the accelerometer, send information to the communication means (if any), and both send and receive information from the CRDS. These communications may be made without physical connections such as wires. Any of the communications may be accomplished wirelessly using signal types including radio and infrared. Common wireless communication protocols include Bluetooth (IEEE 802.15). Wi-Fi (IEEE 802.11), cellular communication protocols, and infrared data association protocols. Embodiments using wireless communications may include components such as transmitters and receivers. Systems may also communicate with other devices or networks, for example a personal computer or the Internet.

Figure 2A:
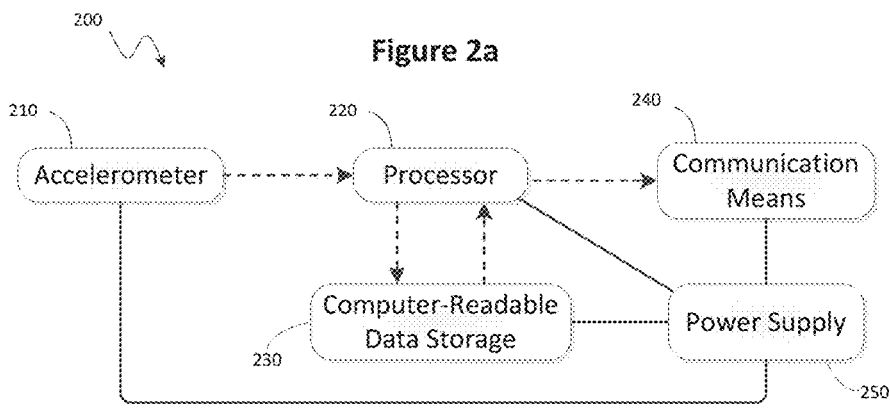
FIGS. 2a-2c are schematic diagrams illustrating systems according to certain embodiments of the present disclosure.
Figure 2B:
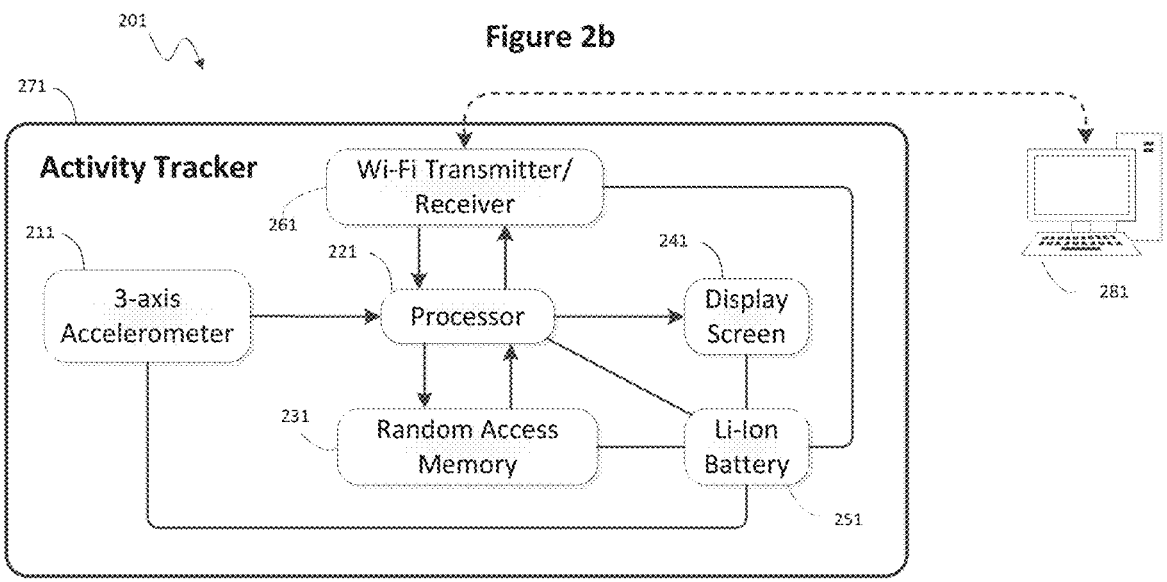
Figure 2C:
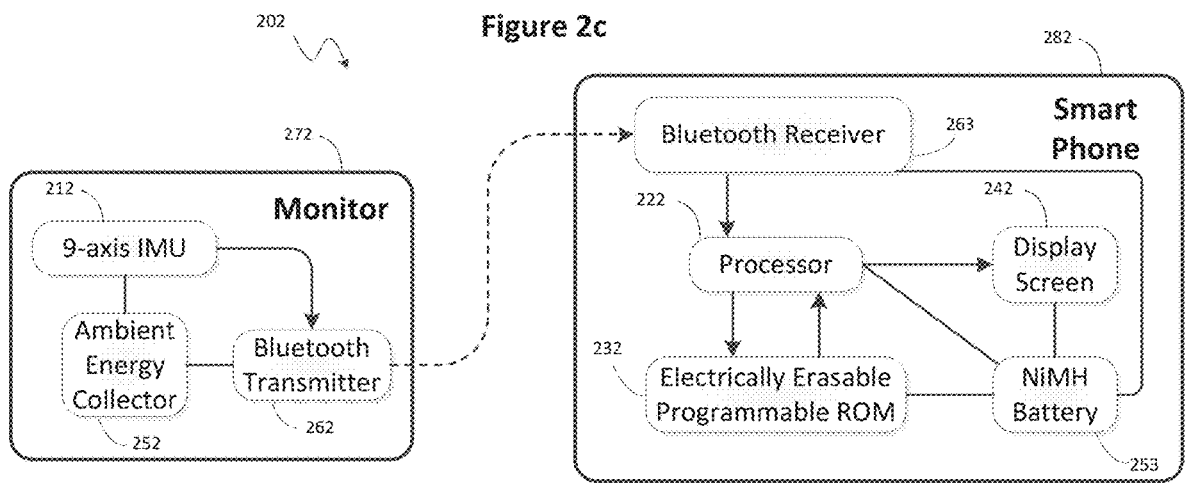

FIGS. 2a through 2c illustrate accelerometer systems for counting steps according to the present disclosure. FIG. 2a illustrates a schematic diagram of the system (200) that includes an accelerometer (210) that transmits outputs to the processor (220). The dashed line connecting the two components indicates that they are communicatively coupled; information may be transferred from one to another, but does not necessarily require a physical connection. The processor (220) executes instructions stored on a computer-readable data storage (CRDS) (230). The processor (220) may store and retrieve data, such as accelerometer data, from the CRDS (230) and processes the data to detect steps. The processor (220) may communicate step data or values derived from the step data to a communication means (240). The components listed above are powered by a power supply (250). While this diagram shows one power supply providing energy to all of the components, the system (200) may use multiple power sources. Any configuration of power sources may be used provided that each component receives power, either directly from a power supply or indirectly through other components.

FIG. 2b illustrates a schematic diagram of a system (201) that may be implemented as a portable, self-contained activity tracker according to certain embodiments. The rectangle surrounding the components (271) indicates that they are all housed in the same device. The activity tracker (271) may include a 3-axis accelerometer (211), a processor configured to function in an activity tracker (221), random access memory (RAM) (231), a display screen (241) visible from the outside of the device, and a rechargeable lithium-ion (Li-Ion) battery (251). The processor (221) performs calculations on the acceleration data and stores any necessary information on the RAM (231). The display (241) may graphically display, among other information, step counts over various time periods. From time to time, the activity tracker (271) may communicate with a second device (281) via radio signals. The activity tracker (271) contains a Wi-Fi transmitter-receiver (261) that exchanges data with the external device (281). This wireless communication allows the activity tracker (271) to transmit unprocessed accelerometer data or step counts to the external device (281) which may be communicatively coupled to networks such as the Internet, and to receive updated instructions.

FIG. 2c illustrates a schematic diagram of a system (202) in which a motion monitor (272) wirelessly communicates accelerometer outputs to an external device (282) for processing, according to certain embodiments. In this embodiment, the external device is a smartphone (282). The motion monitor (272) contains a 9-axis accelerometer/IMU (212), a Bluetooth transmitter (262), and an ambient energy collector (252) to power the other two components. The ambient energy collector (252) may, for example, capture energy from the user's body heat. The Bluetooth transmitter (262) transmits unprocessed accelerometer outputs to a Bluetooth receiver (263) in the smartphone (282). The Bluetooth receiver (263) then relays the accelerometer ouputs to the processor (222) which, in turn, stores and retrieves acceleration data from electrically erasable programmable read-only memory (EEPROM) (232) and determines a step count. The processor (222) then communicates the step count via the display screen (242) on the smartphone (282). The components in the smartphone (282) may be powered by a nickel metal-hydride (NiMH) battety (253).

Figure 3:
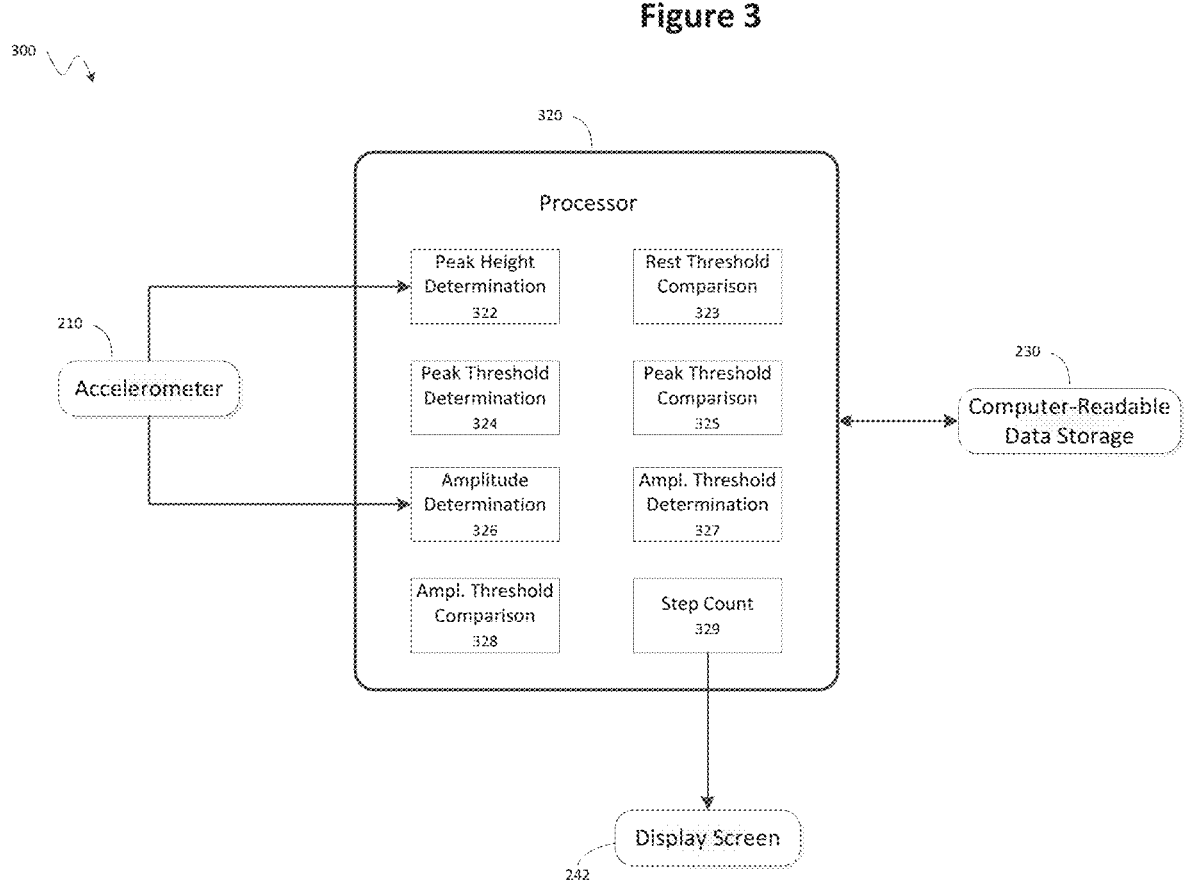
FIG. 3 illustrates a schematic diagram of a system for counting steps according to certain embodiments.

FIG. 3 illustrates a schematic diagram of a system (30X)) for counting steps, according to certain embodiments. An accelerometer (210) transmits acceleration data to the processor (320). The processor (320) stores and retrieves data from a CRDS (230) and may send signals to a display screen (242). The processor (320) comprises circuitry operable to perform steps for determining a step count including determination of peak height for a time period (322), comparison of the peak height to a previously determined rest threshold (323), determination of a peak threshold (324), comparison of the peak height to the peak threshold (325), determination of an amplitude for a time period (326), determination of an amplitude threshold (327), comparison of the amplitude for the time period with the amplitude threshold (328), and determination of a step count (329). Two of the steps, determination of peak height (322) and determination of amplitude (326), may use outputs from the accelerometer (210). Outputs from the accelerometer (210) during a time period may be compared to determine peak height (322), according to a definition of peak height including those discussed herein. Readings from the accelerometer (210) may be compared to determine trough height, according to a definition of peak height including those discussed herein. The processor (320) may then subtract trough height from the peak height from the same time period to determine amplitude (326). Readings from the accelerometer may also be used to determine values such as a rest maximum.

Each of the processor tasks of FIG. 3 may involve communication between the processor (320) and the CRDS (230). Readings for a given time period may be stored on the RDS (230) and accessed by the processor (320) to determine peak height (322). Peak heights and the rest threshold may be stored in the CRDS (230) to allow comparison of the two values (323). Counted peak heights stored on the CRDS (230) may be used by the processor (320) to calculate a peak threshold (324). Comparison of the peak height to the peak threshold (325) may involve storage of the two values being compared on the CRDS (230). Readings from a time period stored on the CRDS (230) may be compared to determine a trough height which, when subtracted from the peak height for the time period, yields the amplitude for the time period (326). Counted amplitudes stored on the CRDS (230) may be accessed by the processor (320) for calculation of the amplitude threshold (327). The processor (320) may compare an amplitude for a time period and the amplitude threshold for the time period stored on the CRDS (230) to determine if the amplitude exceeds the threshold (328). The CRDS (230) may also be used to store a total number of steps. When the processor (320) determines that a step has been taken (329), it may increment the total step count stored on the CRDS (230).

Acceleration Readings from Accelerometer Outputs:

The output of an accelerometer may be analog or digital. Digital accelerometers may produce a binary output of either a high or low voltage and emit outputs at a particular frequency. In some embodiments, the accelerometer output is expressed as a binary number. The output of an analog accelerometer is typically an electrical signal whose voltage is related to the acceleration detected by the accelerometer. As a result, accelerometer outputs may be processed to yield acceleration readings (or simply "readings"). If the output voltage of an accelerometer is directly proportional to the acceleration it experiences, an accelerometer output may simply be multiplied by a coefficient to yield an acceleration reading. If the output voltage is directly proportional to acceleration, the accelerometer output may be treated as the reading itself if the particular units of acceleration are not critical to the purpose of the accelerometer. Thus, in some embodiments, accelerometer outputs function as readings without further processing. If the relationship between accelerometer output and acceleration is non-linear, a function more closely matching the relationship may be used to convert the output into acceleration.

Data Smoothing:

Some embodiments use a type of process referred to as data smoothing. Data smoothing includes a variety of techniques to remove noise from signals and may be applied either before or after accelerometer outputs are converted into readings. However, as used herein, the output of a data smoothing function may be referred to as a reading even if the readings are the input to a data smoothing function. Some embodiments use a low pass filter to remove signal components that are not likely caused by steps. In some embodiments, the low pass filter converts the accelerometer signal from the time domain to the frequency domain using a Fourier transform. Component frequencies too high to be caused by step motion may be removed from the signal in the frequency domain before converting the filtered signal back to the time domain. Some embodiments smooth the accelerometer signal using a moving average in which the reading is a function of an average or weighted average of the n most recent readings. As n increases, the signal becomes increasingly smooth. In some embodiments, n is high enough to remove noise in the signal but low enough that features of interest, such as steps, are not lost. Some embodiments use curve fitting to remove noise from the accelerometer data. Curve fitting creates an equation that approximates the accelerometer signal and the equation outputs are treated as readings.

Definitions of Peak Height and Amplitude:

Peak height and amplitude are two signal features to which thresholds may be applied. As used herein, peak height is the highest reading of the accelerometer within a time period and amplitude is the difference between the highest reading and the lowest reading within a time period. However, different definitions of peak height and amplitude specify different time periods.

Some embodiments have time periods that are of a predetermined length. The length may be the same for all time periods, or time periods may be of different (but still predetermined) lengths. Alternatively, some embodiments have variable time periods that are determined by the data signal. For example, some embodiments set time periods that begin and end each time accelerometer readings increase above a threshold. Some embodiments define time periods as the time between a local maximum and an adjacent local minimum. Time periods may be discrete or continuous. Discrete time periods may be contiguous, separated, or overlapping. Continuous time periods may be described as "sliding windows"-always considering a particular number of readings or readings from a fixed amount of time before a particular reading.

Figure 4A:
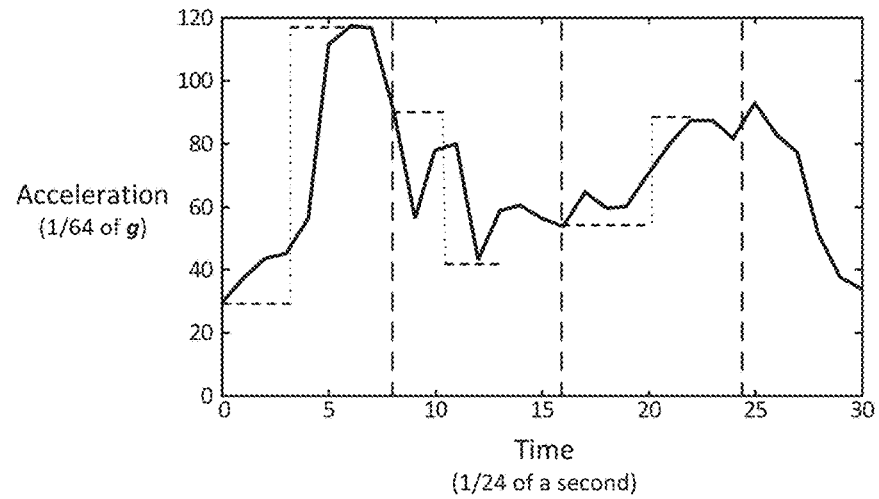
FIGS. 4a-4c illustrate three approaches to defining peak height and amplitude.
Figure 4B:
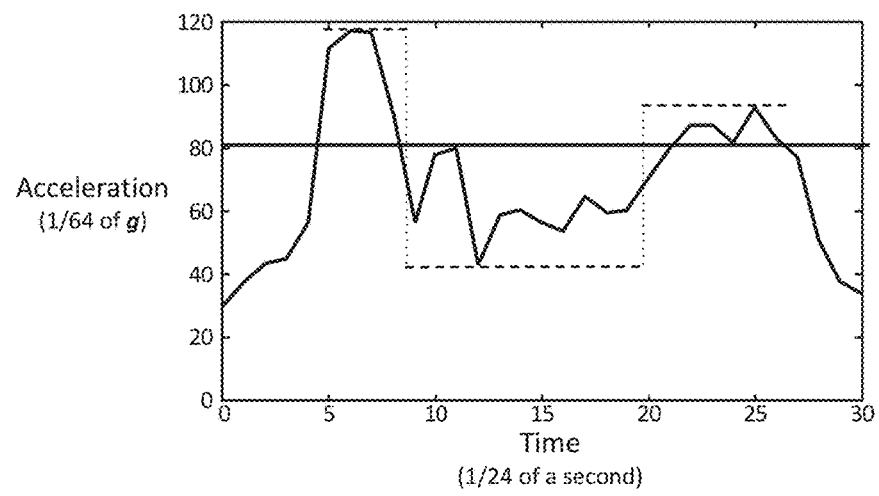
Figure 4C:
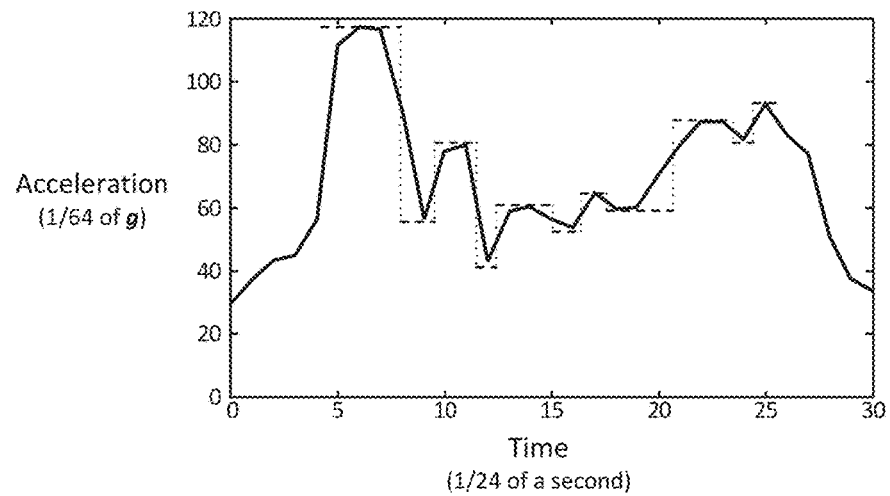

FIGS. 4a-4c illustrate three approaches to defining peak height and amplitude. The time scale on each x axis is in 1/24ths of a second and the units of acceleration on the y axis are 1/64th of g (g=free-fall acceleration in Earth's gravity). FIG. 4a defines peak height and amplitude relative to uniform, contiguous time periods. In this embodiment, the time period is constant and set at 1/3 (8/24) of a second. The boundaries between time periods are represented by the vertical dashed lines. The peak height and the trough height are the highest and lowest points, respectively, within each time period and are represented by horizontal dashed lines. The length of the vertical dotted lines between the peak height and the trough height represents the amplitude for each time period. FIG. 4b illustrates peak height and trough height as defined by a threshold. In this embodiment, the threshold has been set at 80/64 of g. The peak height is the highest point between two threshold crossings that is above the threshold and the trough height is the lowest point between two threshold crossings that is below the threshold. Peak heights and trough height are represented by horizontal dashed lines and the amplitudes are represented by the lengths of the vertical dotted lines. FIG. 4c illustrates the use of local maxima and minima as peak heights and trough heights, respectively. A reading flanked by lower readings on both sides is a local maximum. Conversely, a reading flanked on both sides by higher readings is a local minimum. In this embodiment, an amplitude is the difference in height between a peak height and a directly adjacent trough height. Again, peak heights and trough heights are represented by horizontal dashed lines and amplitudes are represented by the lengths of the vertical dotted lines.

Time Period:

For embodiments that determine peaks and/or troughs according to predetermined time periods, maximum step count is one factor to consider when selecting the length of the time periods. Each time period either increases the step count by one or does not. As time periods become shorter, the potential count over a standard unit of time (such as a minute or hour) increases. For example, dividing time periods into 1/3 of a second allows for a maximum of 180 steps recorded in a minute. Research indicates that 180 steps per minute is approximately the maximum a human could achieve, though most people do not approach this limit. Dividing seconds into halves would allow for a maximum of only 120 steps per minute. Preferred embodiments use time periods of a quarter to three quarters of a second, though embodiments with time periods outside this range may also be useful.

Baseline Readings:

Baseline readings are those readings an accelerometer would be expected to generate when it is at rest. Gravity exerts a force on stationary objects as if they were accelerating at a constant rate. An accelerometer at rest may yield a baseline reading close to g (Earth's gravitational acceleration) if the accelerometer is oriented parallel to the force of gravity. However, a resting accelerometer oriented perpendicular to gravitational force would be expected to yield a baseline reading close to zero. Thus, the baseline reading of an accelerometer at rest is expected to be between zero and g depending on the accelerometer's orientation relative to the force of gravity.

Rest Threshold:

Many accelerometers generate fluctuating readings when they are expected to generate a constant baseline reading. These fluctuations may be due to noise inherent in the accelerometer. Rest thresholds are one way of screening out this inherent noise. A rest maximum is the highest reading that an accelerometer generates when it is at rest for a period of time. The rest maximum may be due to both noise inherent in the accelerometer and the force of gravity.

Figure 5A:
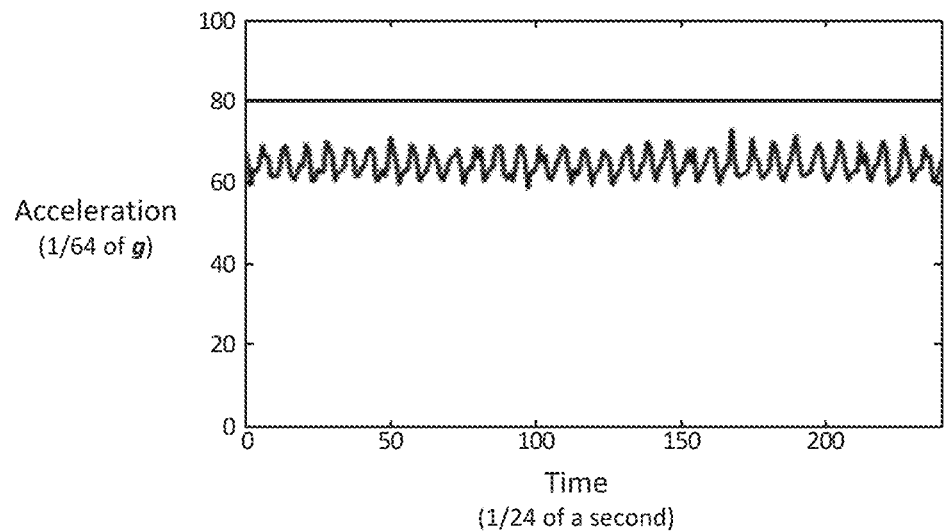
FIGS. 5a and 5b illustrate accelerometer readings at rest.
Figure 5B:
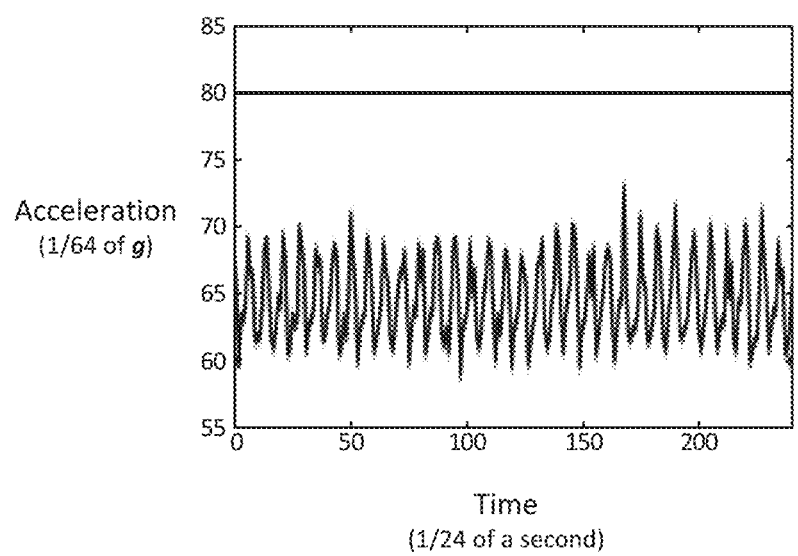

FIGS. 5a and 5b illustrate two views of a data sample collected from an accelerometer at rest for 10 seconds. The time scale on the x axis is in 24ths of a second and the units of acceleration on the y axis are 64ths of g. The primary difference between the two graphs is the scale on the y axis. FIG. 5a has a range from 0 to 100/64 of g while FIG. 5b is magnified to show only the range between 55/64 and 85/64 of g. The average of the readings during these 10 seconds is approximately one (64/64) g. This is due to the force of Earth's gravity on the accelerometer. However, readings fluctuate from as low as 58/64 g to as high as 72/64 g. Thus 72/64 g would be the rest maximum for this particular ten-second sample.

Some embodiments use the unaltered rest maximum as the rest threshold. However, some embodiments set the rest threshold above the rest maximum because the resting accelerometer may only be observed for a finite duration. If the accelerometer were observed for a longer duration, a higher rest maximum would likely be observed. The increase could be achieved in a variety of ways including multiplying the rest maximum by a coefficient greater than one, or by adding a specified amount to it. The rest threshold may be determined once and need not be determined repeatedly. The rest threshold may, for example, be determined at the factory at which the system is manufactured and stored in the CRDS of the system.

Peak Thresholds:

Some embodiments further filter noise by comparing peak heights with a peak threshold. The peak threshold may comprise a function of one or more previous peak heights. In some embodiments, the function is a measure of central tendency applied to two or more previous peak heights. For example, the function may take the mean, median, or a weighted average of two or more previous peaks.

In some embodiments, previous peak heights are the most recent peak heights. Consideration of the most recent peak heights allows the peak threshold to be adjusted for the most recent conditions. Taking a weighted average that weights more recent peaks more heavily further emphasizes the effects of recent changes on the threshold. The peaks need not be the very most recent; taking the average of the first five of the most recent six peaks, for example, would account for very recent peaks without using the most recent one.

Some embodiments use thresholds in combination with other thresholds. When determining a peak threshold, some embodiments calculate a function of only those peak heights exceeding a first threshold. A peak that satisfies one or more criteria for further consideration is referred to a counted peak. When calculating peak thresholds, some embodiments take a function of only two or more counted peaks. In some embodiments, counted peaks comprise only those that exceed the rest threshold. In some embodiments, the threshold is a function of amplitude, discussed herein.

As with the rest threshold, there may be a need to adjust a peak height or threshold to which it is compared. Adjusting the threshold or the peak height can make a test more or less sensitive. Adjusting the peak or peak threshold may be achieved, for example, by multiplying peak height (of either the focal peak or the peaks influencing the threshold to which the focal peak is compared) by a coefficient or adding or subtracting an amount from it. A peak height hat has been adjusted may be referred to as an adjusted peak height. When determining peak thresholds, some embodiments take a function of only two or more adjusted peak heights.

Figure 6:
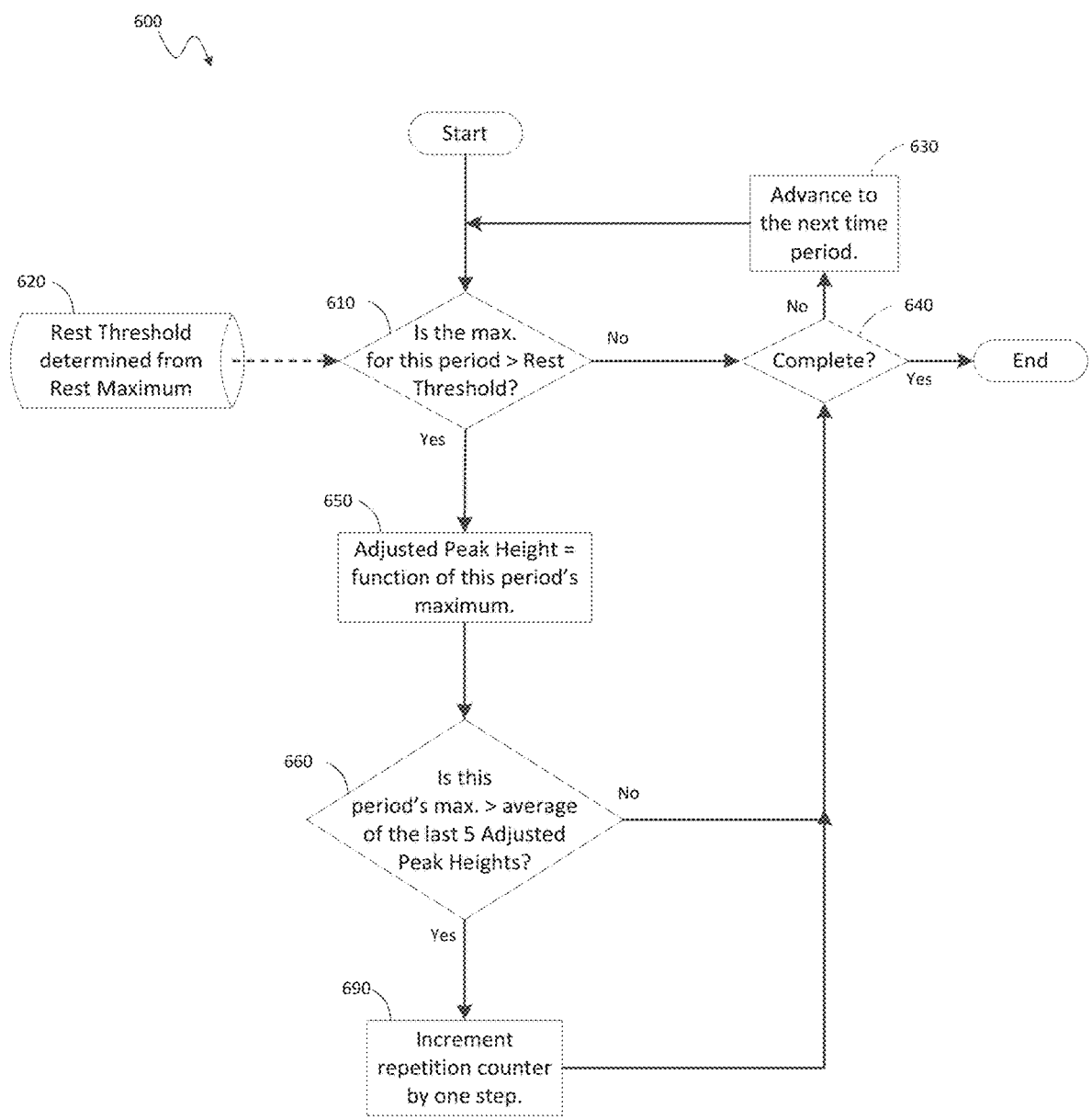
FIG. 6 is a flowchart illustrating a computer-implemented method for counting steps using peak height thresholds according to certain embodiments of the present disclosure.

FIG. 6 illustrates a flowchart of a method (600) of counting steps that applies peak thresholds to accelerometer data, according to certain embodiments. The accelerometer is part of system, such as systems 200-202 and 300, and is communicatively coupled to a processor capable of executing the instructions to process the accelerometer data. The processor first determines whether the maximum reading from a time period is greater than a rest threshold (610). The rest threshold (620) is a function of the rest maximum. The function may, for example, multiply the rest maximum by a coefficient slightly greater than one. The rest threshold (620) may be determined once and need not be determined each time the method (600) is executed. If the maximum reading for the time period is not greater than the rest threshold, processing proceeds to the next time period (630) unless the method (600) is complete (640). If the maximum reading for the time period is greater than the rest threshold, the maximum is referred to as a counted peak height and the processor determines an adjusted peak height as a function of the counted peak height (650). The adjustment function may be, for example, to multiply the peak height by a coefficient or add a fixed value. The method then determines whether the maximum peak height for a given time period is greater than the average of the most recent five adjusted peak heights (660). If not, processing proceeds to the next time period (630) unless the method (600) is complete (640). If the maximum from the time period is greater than the average of the last five adjusted peak heights, a repetition counter is incremented indicating that a step has been taken (690). Then, processing proceeds to the next time period (630) unless the method (600) is complete (640).

Amplitude Thresholds:

Thresholds for amplitude offer another means of filtering noise. The analysis of amplitude parallels the analysis of peak height in many ways. An amplitude from a time period is may be compared to a function of one or more past amplitudes. Embodiments may use, for example, a mean or weighted average of past amplitudes or other measure of central tendency. The amplitudes may be adjusted to make the test more or less sensitive. Adjustments may be made either to the focal amplitude or to one or more past amplitudes influencing the threshold to which the focal amplitude is compared. Adjustments would include multiplying amplitudes by a coefficient or adding or subtracting an amount from an amplitude.

Some embodiments use amplitude thresholds in combination with one or more other thresholds. Some embodiments consider only those amplitudes whose peak heights exceed the rest threshold. Some embodiments use other thresholds to screen the amplitudes that affect the amplitude threshold. For example, some embodiments consider only those amplitudes from time periods for which the peak height exceeds a peak threshold. An amplitude that meets one or more criteria for further consideration may be referred to a counted amplitude. For example, counted amplitudes may be those amplitudes from time periods whose peak heights exceeded a peak threshold. For some embodiments, amplitude thresholds may be a function only of counted amplitudes.

Figure 7:
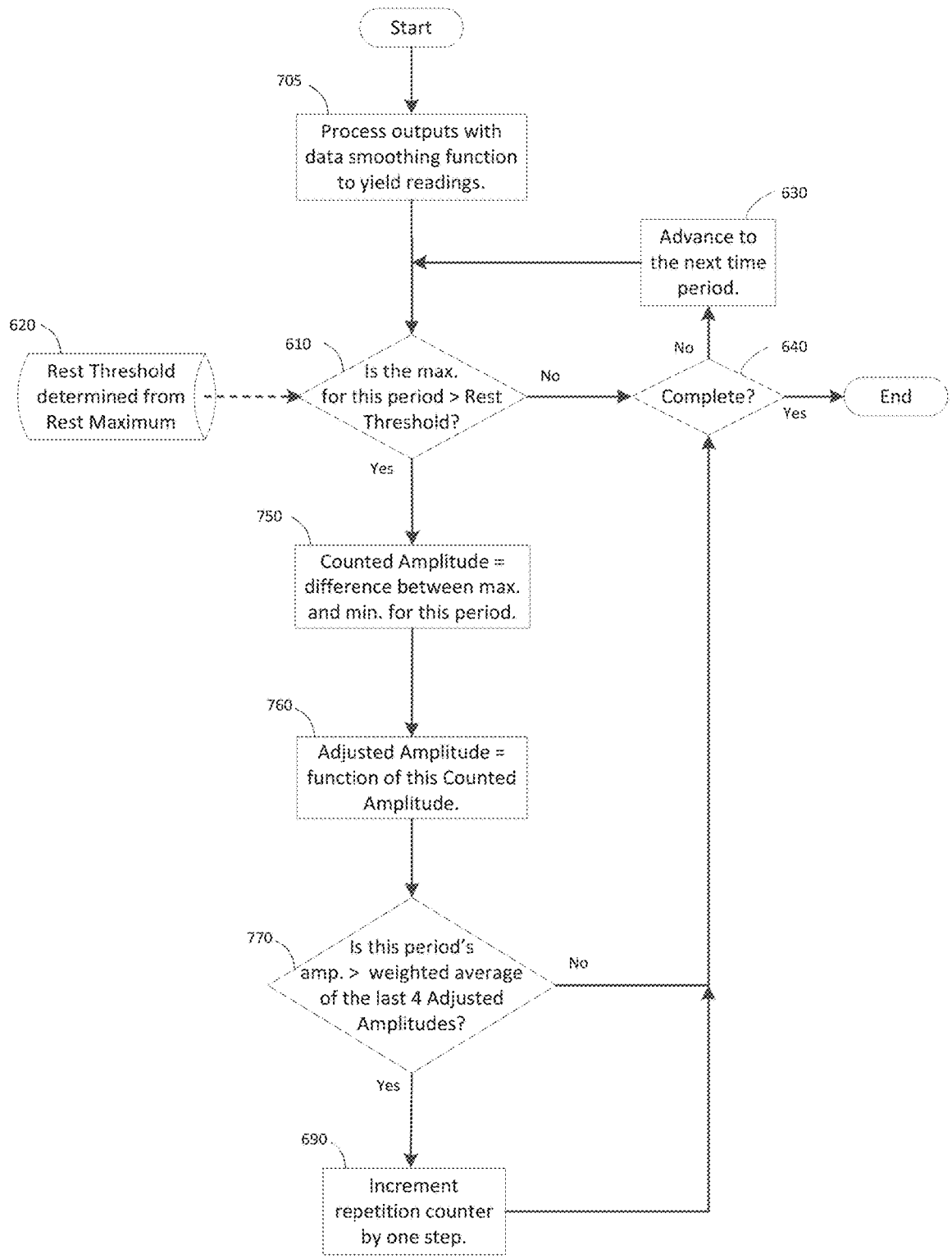
FIG. 7 is a flowchart illustrating a computer-implemented method for counting steps using amplitude thresholds according to certain embodiments of the present disclosure.

FIG. 7 illustrates a flowchart for a method (700) of counting steps that comprises an amplitude threshold in combination with a rest threshold, according to certain embodiments. An accelerometer is part of a system, such as systems 200-202 and 300, and is communicatively coupled to a processor capable of executing the instructions to analyze the accelerometer data. In this embodiment, accelerometer outputs are processed with a data smoothing function to yield readings (705). The processor then determines whether the maximum reading from a time period is greater than a rest threshold (610). The rest threshold (620) is a function of the rest maximum which is the highest reading generated by the accelerometer while it is at rest for a period of time. The rest threshold (620) may be determined once and need not be determined each time the method (700) is executed. If the maximum reading for the time period is not greater than the rest threshold, processing proceeds to the next time period (630) unless the method is complete (640). If the maximum reading for the period is greater than the rest threshold, then the method calculates the difference between the maximum and minimum readings for the time period, the difference referred to as a counted amplitude (750). The adjusted amplitude is a function of the counted amplitude (760). The program then determines whether the amplitude from the time period is greater than the weighted average of the last four adjusted amplitudes (770). If not, processing proceeds to the next time period (630) unless the method is complete (640). If the amplitude is greater than the average of the last four adjusted amplitudes, a repetition counter is incremented indicating that a step has been taken (690). Then, processing proceeds to the next time period (630) unless the method is complete (640).

Combinations of Thresholds:

Thresholds may be used in combination to filter noise from the accelerometer signal. There are multiple ways in which thresholds may be combined. Embodiments with simultaneous combinations simply identify signal features, such as a peak heights or amplitudes, that are greater than the higher of two or more thresholds. In sequential embodiments, one threshold is used as a criterion for inclusion of a value in a function to create a second threshold. A feature that meets one or more criteria is referred to a counted feature. A threshold may be calculated using counted features rather than all features of a particular type.

Additionally, a counted feature may also serve as the metric of interest, such as a step.

Figure 8:
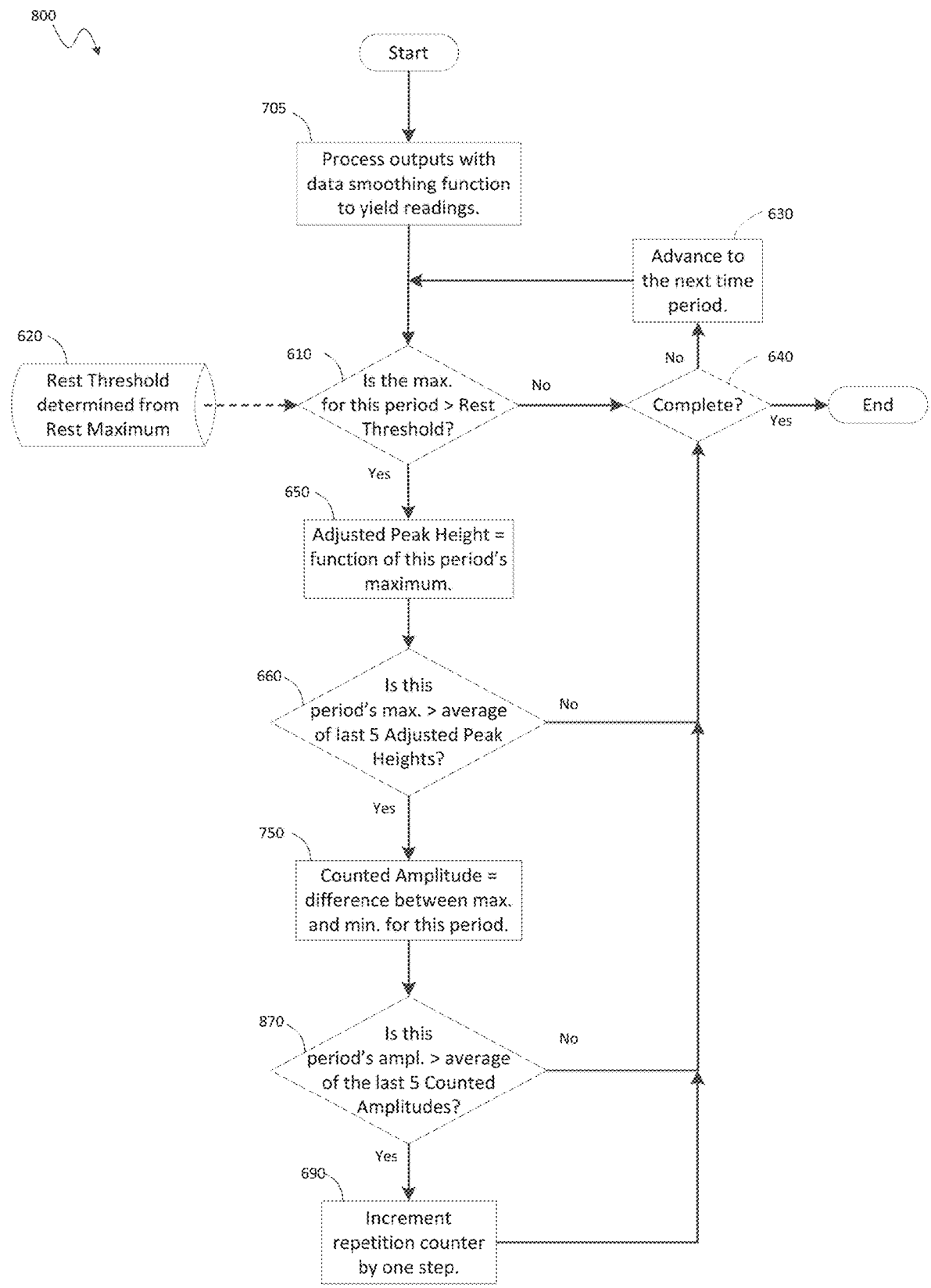
FIG. 8 is a flowchart illustrating a computer-implemented method for counting steps using multiple thresholds according to certain embodiments of the present disclosure.

FIG. 8 illustrates a flowchart of a method (800) for sequentially combining rest, peak height, and amplitude thresholds to count steps, according to certain embodiments. An accelerometer is part of a system, such as systems 200-202 and 300, and is communicatively coupled to a processor capable of executing the instructions to analyze the accelerometer data. In this embodiment, accelerometer outputs are processed with a data smoothing function to yield readings (705). Data smoothing functions could include, for example, a low pass filter, a moving average, or a curve fitting function. The processor then determines whether the maximum reading from a time period is greater than a rest threshold (610). The rest threshold (620) is a function of the rest maximum which is the highest reading generated by the accelerometer while it is at rest for a period of time. The function may, for example, multiply the rest maximum by a coefficient slightly greater than one. The rest threshold (620) may be determined once and need not be determined each time the method (800) is executed. If the maximum reading for the time period is not greater than the rest threshold, processing proceeds to the next time period (630) unless the method (800) is complete (640). If the maximum reading for the time period is greater than the rest threshold, then the program identifies the maximum as a counted peak height and then executes a function of the counted peak height, the output of the function referred to an adjusted peak height (650). The processor then determines whether the maximum peak height for the time period is greater than the average of the last five adjusted peak heights (660). If not, processing proceeds to the next time period (630) unless the method (800) is complete (640). If the maximum from the time period is greater than the average of the last five adjusted peak heights, then the processor calculates a counted amplitude as the difference between the maximum and minimum readings for the time period (750). In some embodiments, the amplitude may be adjusted by a function. The processor then determines whether the amplitude from the time period is greater than the average of the last five counted amplitudes (870). If not, processing proceeds to the next time period (630) unless the method (800) is complete (640). If the amplitude is greater than the average of the last five counted amplitudes, a repetition counter s incremented indicating that a step has been taken (690). Then, processing proceeds to the next time period (630) unless the method (800) is complete (640).

Figure 9:
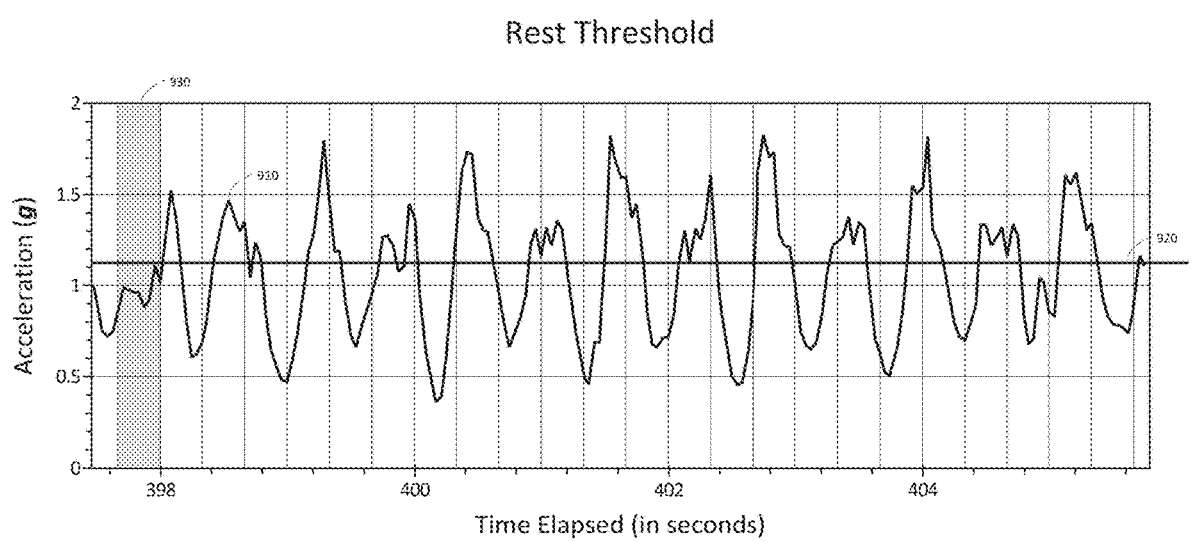
FIG. 9 illustrates a rest threshold applied to segments of an accelerometer signal according to certain embodiments of the present disclosure.
Figure 10:
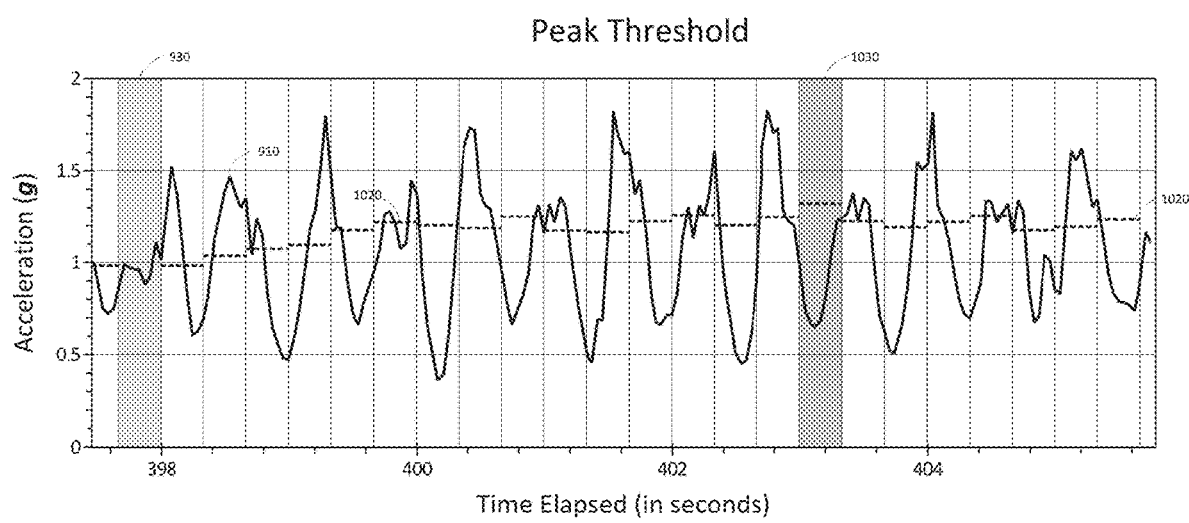
FIG. 10 illustrates a peak threshold applied to segments of an accelerometer signal that have exceeded a rest threshold according to certain embodiments of the present disclosure.
Figure 11:
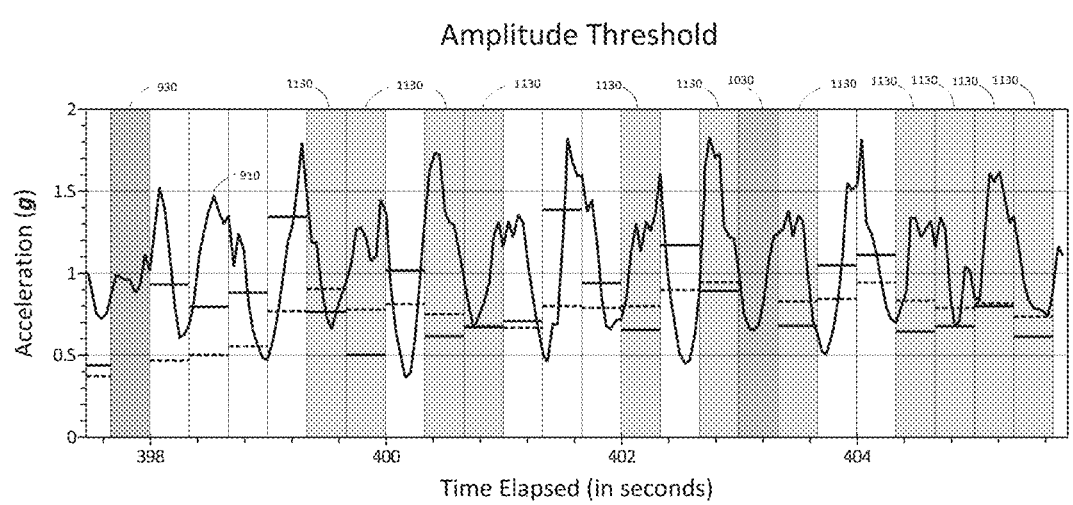
FIG. 11 illustrates an amplitude threshold applied to segments of an accelerometer signal that have exceeded both a peak threshold and a rest threshold according to certain embodiments of the present disclosure.

FIGS. 9, 10, and 11 include data plots illustrating how the method of FIG. 8 would be applied to a sample of accelerometer data collected over 8 seconds. The x-axis in each plot represents time in seconds and time is partitioned into contiguous periods of one third (⅓) of a second as represented by the black vertical lines. The y-axis represents acceleration in g (free fall acceleration in Earth's gravity). The wavy signal line (910) represents the accelerometer reading at each point in time. In this embodiment, peak height is defined as the highest reading in each time period and the amplitude is the difference between the highest and lowest points in each time period.

FIG. 9 illustrates the application of a rest threshold to a segment of accelerometer data, according to certain embodiments. In this embodiment, the rest threshold has been set at 1.12 g and is represented by the horizontal line (920) at that level. Any time period in which the signal line does not exceed the rest threshold is eliminated from consideration for either a step or calculation of subsequent thresholds. In this particular data segment, the first full time period (930) was the only time period in which the signal did not exceed the rest threshold. Time period 930 is shaded to indicate that it has been eliminated from consideration, both for being counted as a step and in the calculation of subsequent thresholds. The remainder of the peaks are referred to as counted peaks.

FIG. 10 illustrates the application of a peak threshold to the data segment (910) after the application of a rest threshold, according to certain embodiments. The horizontal dashed line in each time period (e.g. 1020) represents the peak threshold for that period. Each peak threshold is the mean of the last five counted peak heights each of which has been adjusted by multiplying by a coefficient. Because the peak height in the first full time period (930) did not exceed the rest threshold, the peak height for that time period is not incorporated in any of the averages. In this data segment (910), the first time period after second 403 (1030) is the only time period in which the peak height did not exceed its peak threshold. Time period 1030 is shaded to indicate that it has been eliminated from consideration both as a step and for calculation of amplitude thresholds. Thus, there are two time periods from this data segment that are not be considered for the amplitude threshold.

FIG. 11 illustrates the application of an amplitude threshold to a data segment (910) after the application of a peak threshold and a rest threshold, according to certain embodiments. Each of the remaining time periods not disqualified by the first two thresholds contains two horizontal lines. The solid horizontal line represents the amplitude for the time period in which it is shown—the difference between the highest and lowest points in the time period. The dashed horizontal line represents the amplitude threshold for the time period in which it is shown. The amplitude threshold is the average of the last five counted amplitudes. The time periods whose amplitudes did not exceed the amplitude threshold (1130) are shaded gray (in addition to the time periods that did not pass the peak threshold (1030) and rest threshold (930)). In the data from this time period (910), 11 of the 24 time periods passed all three thresholds. Thus, eleven steps are recorded for the eight seconds of data.

Implementation of Use:

As explained in the Background section, a single fixed threshold may not accurately count steps of different individuals or of a single individual in different circumstances. One situation in which the intensity of an individual's steps may change over time involves the healing of post-surgical patients. Research has shown that post-surgical activity, ambulation in particular, may increase the rate at which patients heal. After surgery, patients may be weak and are often in pain. Jarring, high-acceleration steps may increase their pain, particularly at incision sites. Therefore, soon after surgery, patients often take steps that create only low levels of acceleration, sometimes referred to as the "hospital shuffle." Commercial activity trackers designed to promote athletic fitness have failed to detect steps of the hospital shuffle. Correspondingly, activity trackers with a lower fixed threshold that can detect steps of the hospital shuffle have over-counted steps of healthy individuals.

As patients heal after surgery, the intensity of their steps often increases as pain decreases and their strength returns. Accordingly, implementations of the present disclosure may provide systems and devices that detect steps of varying intensity. This enables a single device that dynamically changes its sensing thresholds to detect a user's steps. For instance, after surgery, a device according to the present disclosure may detect steps of the hospital shuffle with a set of thresholds that are low due to the surrounding acceleration readings. As the intensity of a patient's steps increases, the step thresholds increase according to the increased magnitude of acceleration readings caused by the increasingly vigorous steps.

In the context of a post-surgical walking program, it is advantageous to provide each patient with a single device rather than exchanging devices as the intensity of their steps increases. To further complicate matters, patients may recover at different rates, so the timing at which an exchange would be needed may vary. A single device that changes thresholds for step detection allows a program to issue a single device that accurately counts steps throughout the progression of the patient's recovery.

The above description of the invention is neither exclusive nor exhaustive and is intended neither to describe all possible embodiments (also referred to as "examples") of the invention nor to limit the scope of the invention. Embodiments of the invention may include elements in addition to those in the described embodiments and, in some cases, may contain only a subset of the elements described in a particular embodiment. Embodiments may contain any combination of elements in the described embodiments in addition to elements not expressly described. As used herein, the articles "a" and "an" may include one or more than one of the oun modified by either without respect to use of other phrases such as "one or more" or "at least one." The word "or" is used inclusively unless otherwise indicated. Terms such as "first," "second," "third" and so forth are used as labels to distinguish elements and do not indicate sequential order unless otherwise indicated. In addition to the embodiments described above, embodiments of the invention include any that would fall within the scope of the claims, below.

What is claimed is:

1. A system for counting steps, the system comprising:
   an accelerometer coupled to an individual, the accelerometer generating accelerometer outputs;
   a processor in communication with the accelerometer; and
   a non-transitory computer readable medium in communication with the processor, the non-transitory computer-readable medium storing instructions controlling the processor to:
      determine readings using the accelerometer outputs;
      identify counted amplitudes, each of the counted amplitudes comprising a difference between a maximum reading and a minimum reading during a time period in which the maximum reading exceeds a rest threshold, the rest threshold determined by:
         receiving readings from the accelerometer during a period of rest,
         identifying a rest maximum, the rest maximum comprising a greatest reading generated by the accelerometer during the period of rest, and
         determining the rest threshold using the rest maximum;
      determine an amplitude threshold for each time period having a counted amplitude, the amplitude threshold comprising a first weighted average of two or more counted amplitudes;
      identify counted peak heights, each of the counted peak heights comprising the maximum reading during a time period in which the amplitude is greater than the amplitude threshold;
      determine a peak threshold for each time period having a counted peak height, the peak threshold comprising a first weighted average of two or more counted peak heights; and
      increment a counter if the counted peak height exceeds the peak threshold associated with the time period in which the counted peak height occurred, a number stored by the counter representing the number of steps taken by the individual.

2. The system of claim 1, wherein the accelerometer measures linear acceleration along three axes and the accelerometer outputs from the three axes are combined.

3. A method of counting steps from accelerometer outputs of an accelerometer, the accelerometer coupled to an individual and in communication with a processor, the processor in communication with a non-transitory computer readable medium, the non-transitory computer readable medium storing instructions controlling the processor to execute the steps of the method, the method comprising:
   determining readings using the accelerometer outputs of the accelerometer;
   identifying counted amplitudes, each of the counted amplitudes comprising a difference between a maximum reading and a minimum reading during a time period in which the maximum reading exceeds a rest threshold, the rest threshold determined by:
      receiving readings from the accelerometer during a period of rest,
      identifying a rest maximum, the rest maximum comprising a greatest reading generated by the accelerometer during the period of rest, and
      determining the rest threshold using the rest maximum;
   determining an amplitude threshold for each time period having a counted amplitude, the amplitude threshold comprising a first weighted average of two or more counted amplitudes;
   identifying counted peak heights, each of the counted peak heights comprising the maximum reading during a time period in which the amplitude is greater than the amplitude threshold;
   determining a peak threshold for each time period having a counted peak height, the peak threshold comprising a first weighted average of two or more counted peak heights; and
   incrementing a counter if the counted peak height exceeds the peak threshold associated with the time period in which the counted peak height occurred, a number stored by the counter representing the number of steps taken by the individual.

4. The method of claim 3, wherein the accelerometer measures linear acceleration along three axes and the accelerometer outputs from the three axes are combined.

5. A computer program product for counting steps from accelerometer outputs of an accelerometer, the accelerometer coupled to an individual and in communication with a processor, the processor in communication with computer program product, the computer program product comprising at least one non-transitory computer-readable storage medium having computer-readable program code portions stored therein, the computer-readable program code portions, when executed, configured to:
   determine readings using the accelerometer outputs;
   identify counted amplitudes, each of the counted amplitudes comprising a difference between a maximum reading and a minimum reading during a time period in which the maximum reading exceeds a rest threshold, the rest threshold determined by:
      receiving readings from the accelerometer during a period of rest, identifying a rest maximum, the rest maximum comprising a greatest reading generated by the accelerometer during the period of rest, and determining the rest threshold using the rest maximum;

determine an amplitude threshold for each time period having a counted amplitude, the amplitude threshold comprising a first weighted average of two or more counted amplitudes;

identify counted peak heights, each of the counted peak heights comprising the maximum reading during a time period in which the amplitude is greater than the amplitude threshold;

determine a peak threshold for each time period having a counted peak height, the peak threshold comprising a first weighted average of two or more counted peak heights; and increment a counter if the counted peak height exceeds the peak threshold associated with the time period in which the counted peak height occurred, a number stored by the counter representing the number of steps taken by the individual.

6. The computer program product of claim 5, wherein the accelerometer measures linear acceleration along three axes and the accelerometer outputs from the three axes are combined.

\* \* \* \* \*